United States Patent

Fuchs et al.

[11] 4,007,192
[45] Feb. 8, 1977

[54] NAPHTHALIMIDE-4,5-DICARBOXYLIC ACIDS

[75] Inventors: Otto Fuchs, Frankfurt am Main; Adolf Kroh, Munster, Oberlahnkreis, both of Germany

[73] Assignee: Hoechst Aktiengesellschaft, Frankfurt am Main, Germany

[22] Filed: Sept. 13, 1974

[21] Appl. No.: 505,624

Related U.S. Application Data

[62] Division of Ser. No. 398,410, Sept. 18, 1973, abandoned.

[30] Foreign Application Priority Data

Sept. 20, 1972 Germany .......................... 2246111

[52] U.S. Cl. .................. 260/281 F; 260/281 N
[51] Int. Cl.[2] ............. C07D 217/24; C07D 491/06
[58] Field of Search ............... 260/281 A, 281 F

[56] References Cited

UNITED STATES PATENTS 2,835,674   5/1958   Eckart ........................... 260/281

FOREIGN PATENTS OR APPLICATIONS 1,955,070   5/1971   Germany
2,246,111   4/1974   Germany

OTHER PUBLICATIONS

Gerasimenko, Yu E., et al., Chem. Abs. 69, 51997n (1967).

*Primary Examiner*—Donald G. Daus
*Assistant Examiner*—Mark L. Berch
*Attorney, Agent, or Firm*—Curtis, Morris & Safford

[57] ABSTRACT

Novel naphthalimide-4,5-dicarboxylic acids of the general formula

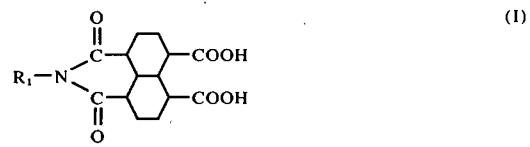

(I)

or the anhydrides thereof, wherein $R_1$ is hydrogen, hydroxy, amino, alkyl having 1 to 8 carbon atoms, hydroxyalkyl, alkoxyalkyl, aminoalkyl, monoalkylaminoalkyl, hydroxyalkoxyalkyl, alkoxyalkoxyalkyl, carbalkoxyalkyl, carboxyalkyl or phenylalkyl having each 1 to 6, preferably 1 to 4 carbon atoms in the alkyl or alkoxy portion or phenyl substituted by 1 to 3 halogen atoms, amino, alkyl, alkoxy, acylamino, acyl having each 1 to 4 carbon atoms, benzoyl or Carboxyl, and a process for preparing them, wherein naphthalene-1,4,5,8-tetracarboxylic acid, the mono- or dianhydride thereof are reacted as alkali salts in an aqueous solution with amines of the formula $H_2N - R_1$   (II)

wherein $R_1$ has the above meaning, at a pH-value of 5.2 – 7.5, preferably of 5.4 – 6.4, at temperatures of 80 to 160° C.

1 Claim, No Drawings

NAPHTHALIMIDE-4,5-DICARBOXYLIC ACIDS

This is a division of application Ser. No. 398,410 filed Sept. 18, 1973, now abandoned.

The preparation of two naphthalimide-4,5-dicarboxylic acids is known from German Patent Specification No. 553,629 and German Offenlegungsschrift No. 2,000,623.

Thus, Example 7 of German Reichspatent No. 553,629 describes the preparation of N-phenyl-naphthalimide-4,5-dicarboxylic acid by dissolving naphthalene-1,4,5,8-tetracarboxylic acid in water with the aid of potassium carbonate and heating it to the boil for some time together with aniline. However, the reaction is not complete. On testing this process it has appeared that the N-phenyl-naphthalimide-4,5-dicarboxylic acid, when acidified carefully, is not precipitated in pure form, but in mixture with the potassium salt thereof. The presence of rather large portions of potassium salt in the mixture explains that the melting point of the reaction product could not exactly be measured. The pure acid, however, melts at 318° C. If instead of aniline according to this Example other amines are used in equivalent amounts, the reaction is not quantitative either, and an expensive working-up to obtain the imide and to recover the naphthalene-tetracarboxylic acid not reacted is required.

Furthermore, it is known from German Patent Specification No. 1,005,969 that naphthalene-tetracarboxylic acid can be reacted in an aqueous solution in the presence of big amounts of buffer substances and salts with ortho-phenylene-diamines to give the corresponding naphthoylene-arylimidazol-peridicarboxylic acids. This known process is carried out with large amounts of liquid. Furthermore, the condensation products crystallizing during the reaction are not obtained in a completely pure form and their purification and conversion into the free acid require an expensive working-up. If the principle of this known process, which is limited to the reaction with orthodiamines, is applied to monoamines, the reaction to give the corresponding imides is not quantitative under the conditions indicated therein. Due to the high salt concentration the products obtained are mostly precipitated so that they cannot be applied directly for the purpose mentioned below and would have to be subjected also to a previous expensive working-up.

From German Offenlegungsschrift No. 2,000,623 it is known that N,N-dimethyl-1,3-diamino-propane can be condensed with naphthalene-tetracarboxylic acid or the anhydride thereof either in about 30 times the amount of dimethyl formamide or in 30 times the amount of water, to give the corresponding monoimide. With the process carried out in dimethyl formamide the yield is only about 53% of the theory. Furthermore, the process has the disadvantage that large amounts of organic solvents must be used. The process carried out in water which essentially corresponds to Example 1 of German Patent No. 1,005,969, with the difference that instead of the orthophenylene-diamine the corresponding amount of N,N-dimethyl-1,3-diamino-propane is used, has the same disadvantages described above. The monoimide is separated as hydrochloride with a yield of only about 77% of the theory.

The present invention relates to novel naphthalimide-4,5-dicarboxylic acids of the general formula

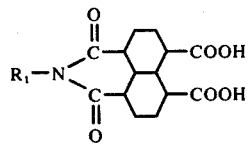

or the anhydrides thereof, wherein $R_1$ is hydrogen, hydroxy, amino, alkyl having 1 to 8 carbon atoms, hydroxyalkyl, alkoxyalkyl, aminoalkyl, monoalkylaminoalkyl, hydroxyalkoxyalkyl, alkoxyalkoxyalkyl, carbalkoxyalkyl, carboxylalkyl or phenylalkyl having each 1 to 6, preferably 1 to 4 carbon atoms in the alkyl or alkoxy portion or phenyl substituted by 1 to 3 halogen atoms, amino, alkyl, alkoxy, acylamino, acyl having each 1 to 4 carbon atoms, benzoyl or carboxyl.

The invention further relates to a process for preparing these naphthalimide-4,5-dicarboxylic acids, wherein naphthalene-1,4,5,8-tetracarboxylic acid, the mono- or dianhydride thereof are reacted as alkali salts in an aqueous solution with amines of the formula $$H_2N - R_1 \quad (II)$$

wherein $R_1$ has the above meaning, at a pH-value of 5.2 – 7.5, preferably of 5.4 – 6.4, at temperatures of 80° to 160° C.

These novel compounds can be prepared in a simple way by suspending 1 mol of the 1,4,5,8-naphthalene-tetracarboxylic acid, generally available as a semianhydride, in 12 to 20 times the amount of water, heating the suspension to 60°–95° C and dissolving the naphthalene-tetracarboxylic acid with the 2 to 6-molar amount of sodium or potassium hydroxide solution. Then the pH-value was adjusted to about 5.0 –5.6 with phosphoric acid or acetic acid, and the calculated amount of the amine of the general formula $R_1$-NH$_2$ is added in a slight excess of up to 10%, the pH-value being adjusted to 5.2 – 7.5. Then the condensation reaction is carried out at an elevated temperature, either under reflux or in a closed reaction vessel at a temperature of preferably 100° to 135° C during 2 to 6 hours, preferably 3 to 5 hours. During this period the naphthalene-tetracarboxylic acid is reacted quantitatively with the amine. Particularly when using aliphatic amines, the condensation product obtained as alkali salt is easily soluble in the reaction solution in the heat and can be easily freed, by simple filtration, from the corresponding naphthaline-tetracarboxylic acid diimide undissolved and formed simultaneously in a small amount. By acidifying the clarified solution with mineral acid, filtering the deposit formed and subsequently drying, the corresponding naphthalimide-4,5-dicarboxylic acids are obtained in a pure form and in very high to practically quantitative yields.

The free naphthalimide-dicarboxylic acids can be converted in known manner into the corresponding anhydrides, for example by heating in a high-boiling solvent, such as trichlorobenzene or α-chloro-naphthalene, while distilling off the water set free in the heat. By rapid vatting in alkaline sodium dithionite solutions the imide anhydrides according to the invention show a characteristic pure blue vat color.

In the cases in which, during condensation, less well-soluble alkali salts are formed, which are no longer completely soluble in the reaction solution in the heat, the reaction solution is acidified with mineral acid and the imide-dicarboxylic acids precipitated are isolated.

To separate from the unsoluble diimide which has also formed, the moist crude product is suspended in water, the imidedicarboxylic acid is dissolved in the heat by addition of sodium carbonate solution and the diimide is separated by filtration. In the same way as described above the imidedicarboxylic acid is isolated. In this working-up care must be taken that the pH-value of the solution is not considerably above 8.0 after addition of the soda solution, since the naphthalimide-4,5-dicarboxylic acids are saponified very easily to give the naphthalene-tetracarboxylic acid. This fact is unusual since most of the naphthalimides are very resistant to alkalis in the heat and can be saponified only with difficulty.

Amines which are used for the condensation with naphthalene-tetracarboxylic acid are for example: ammonia, hydroxyl amine, hydrazine, straight-chained and branched alkyl amines such as methyl-, ethyl-, propyl-, butyl-, hexylamine, isopropyl-, isobutyl-, 2-ethyl-hexylamine; straight-chained and branched alkyl amines substituted by hydroxy and/or alkoxy groups, such as amino-ethanol, aminopropanol, 2-amino-i-butanol, methoxyethylamine, methoxypropylamine, ethoxypropylamine, isopropoxy-propylamine, n-butoxy-propylamine, 3-($\Omega$-ethoxy)ethoxy-propylamine, 3-($\Omega$-hydroxy)-ethoxy-propylamine; alkylamines substituted by carboxyl groups, such as aminoacetic acid, 3-amino-propionic acid, 4-amino-butyric acid as well as the alkyl esters thereof; alkyl amines substituted by phenyl such as benzyl amine or phenyl-ethyl-amine as well as mono- or dichloro-anilines, toluidines, xylidines, anisidines, phenetidines, amino-benzoic acids and the alkyl esters thereof, m- and p-phenylene-diamines and the monoacylic compounds, amino-acetophenone or aminobenzophenone.

The new naphthalimide-4,5-dicarboxylic acids are valuable intermediate products for the preparation of dyestuffs. Particularly interesting are the products which contain an alkyl, hydroxy-alkyl or alkoxyalkyl group, since they make possible without an intermediate isolation of the naphthalimide-4,5-dicarboxylic acids and an expensive purification, to prepare in a particularly economical way valuable dispersion dyestuffs for example those of the naphthoylene-arylimidazolperi-dicarboxylic acid imide series, for dyeing synthetic fibres on the basis of polyester, polyacrylonitrile, cellulose acetate as well as polyamide.

The process of the present invention provides in a very economical way high yields of naphthalimide-4,5-dicarboxylic acids, which are free from naphthalene-tetra-carboxylic acid.

According to the state of the art it has been surprising that, when maintaining determined pH-conditions, a quantitative reaction of naphthalene-tetracarboxylic acid takes place in an aqueous solution with mono-amines.

The following Examples illustrate the invention.

EXAMPLE 1:

20 Grams of naphthalene-1,4,5,8-tetracarboxylic acid-semianhydride were suspended in 300 ml of water and stirred at 70° C with 34 g of a 33% sodium hydroxide solution. After 10 minutes a pH-value of 5.1 to 5.3 was adjusted with 10.65 g of a 80% phosphoric acid; after addition of 6.6 g of 3-methoxy-n-propyl-amine the solution obtained had a pH-value of 5.9 to 6.1. The reaction solution was heated for 3 hours to 125° – 130° C. By filtration at 60 to 80° C the naphthalenetetracarboxylic acid diimide formed in small amounts was separated, the filtrate was adjusted with hydrochloric acid to a pH-value of 2 and stirred for 30 minutes at 80° C. The N-(3'-methoxy-n-propyl)-naphthalimide-4,5-dicarboxylic acid precipitated was suction-filtered in the cold, washed free from salt with cold water and dried. Yield: 94% of the theory.

To convert into the anhydride 15 g of the imidedicarboxylic acid obtained were suspended in 150 g of α-chloronaphthalene; the suspension was heated up to 250° C and allowed to stand for 5 hours at this temperature, while stirring. After cooling, the crystalline, nearly colorless N-(3'-methoxy-n-propyl)-naphthalimide-4,5-dicarboxylic acid anhydride was suction-filtered, washed with benzene and dried. Melting point: 214° C.

EXAMPLE 2:

If - in analogy to Example 1 - naphthalene-1,4,5,8-tetracarboxylic acid-semianhydride was reacted with 5.4 g of isobutyl-amine instead of with 3-methoxy-n-propylamine, the N-isobutyl-naphthalimide-4,5-dicarboxylic acid was obtained in a yield of 96% of the theory.

The melting point of the anhydride prepared according to the process of Example 1 was at 257° C.

EXAMPLE 3:

In analogy to the method described in Example 1, the N-(3'-butoxy-n-propyl)-naphthalimide-1,4,5,8-dicarboxylic acid was obtained in a yield of 90% of the theory by reaction of 20 g of naphthalene-1,4,5,8-tetracarboxylic acid-semianhydride with 10.4 g of 3-butoxy-n-propylamine. Melting point of the anhydride: 149° C.

EXAMPLE 4:

50 Grams of naphthalene-1,4,5,8-tetracarboxylic acid semianhydride were suspended in 1000 ml of water; at 95° C this suspension was mixed with 42.5 g of a 33% sodium hydroxide solution and stirring was continued for 30 minutes. 16.5 Grams of 3-methoxy-n-propylamine and 3 g of phosphoric acid (85%) were added, and a pH-value of 5.7 to 5.8 was adjusted. The solution obtained was heated for 5 hours in a closed vessel, while stirring at 125° to 130° C. After cooling to 70 – 80° C it was filtered from the naphthalene-tetracarboxylic acid-di(N-methoxy-propyl)-imide formed in only small amounts, the filtrate was adjusted to pH 1.5 – 2.0 with hydrochloric acid and stirring was continued for 30 minutes at 80° C.

The N-(3'-methoxy-n-propyl)-naphthalimide-4,5-dicarboxylic acid precipitated was suction-filtered in the cold, washed free from salt with cold water and dried. Yield: 94 % of the theory. Melting point of the anhydride: 214° C.

EXAMPLE 5:

106 Grams of naphthalene-1,4,5,8-tetracarboxylic acid were suspended in 1500 ml of water at 80° C and dissolved by addition of 170 g of a 33% sodium hydroxide solution. Then 48 g of glacial acetic acid were added while stirring, and stirring was continued for 10 minutes. After addition of 33 g of 3-methoxy-n-propylamine a pH-value of 5.8 was adjusted and the reaction solution was heated for 5 hours to 125° – 130° C. The N-(3'-methoxy-n-propyl)-naphthalimide-4,5-dicarboxylic acid was isolated as in Example 4. Yield:

93% of the theory. Melting point of the anhydride: 214° C.

EXAMPLE 6:

50 Grams of naphthalene-1,4,5,8-tetracarboxylic acid-semianhydride were suspended in 750 ml of water and dissolved at 80° C by addition of 98 g of a 40% by weight solution of potash. After addition of 25 g of phosphoric acid (85% by weight) and 16.5 g of 3-methoxy-n-propylamine, a pH-value of 5.8 to 6.1 was adjusted; the solution was heated to 130° C and stirred for 5 hours at this temperature. After cooling to 90° C, the potassium salt, partly precipitated, of the N-(3'-methoxypropyl)-naphthalimide-4,5-dicarboxylic acid was adjusted to an acidic range with hydrochloric acid; the stirring of the solution was continued for 30 minutes at 80° – 90° C. The crystalline precipitation obtained was suction-filtered in the cold and washed free from salt with water.

The moist press-cake was dissolved in 700 ml of water at 70° C with a 10% sodium carbonate solution and the solution obtained had a pH-value of about 7.0 to 7.5. The naphthalenetetracarboxylic acid-di-(methoxy-propyl)-imide undissolved and formed in small amounts was separated by filtration. The filtrate was adjusted to pH 2 with hydrochloric acid, and stirring was continued at 70°– 80° C for 30 minutes. The N-(3'-methoxy-n-propyl)-naphthalimide-4,5-dicarboxylic acid precipitated was suction-filtered cold, washed free from salt with cold water and dried. Yield: 94% of the theory. Melting point of the anhydride: 214° C.

EXAMPLE 7:

50 Parts by weight of the naphthalene-1,4,5,8-tetracarboxylic acid-semianhydride were suspended in 750 parts by weight of water at 70° C; 85 parts by weight of sodium hydroxide solution (33% by weight) were added. After stirring for 10 minutes, about 25 parts by weight of phosphoric acid (85% by weight) were added to the solution thus obtained, and a pH-value of 5.2 was adjusted. After introducing, while stirring, 20.3 parts by weight of benzyl amine, the whole was heated, while stirring in the closed vessel, to 140°–145° C and the reaction was finished during 4.5 hours at this temperature. After cooling to 80° C the reaction product which has partly precipitated, was completely precipitated by adding 45 parts by weight of hydrochloric acid, (36%), suction-filtered at room temperature and washed neutral with water. The moist press-cake was suspended in 2000 parts by weight of water at 80° C and dissolved with a sodium carbonate solution (10%) at a pH-value of 7. The undissolved naphthalene-tetracarboxylic acid-di-(benzyl)-amide formed in a small amount was filtered, the filtrate was adjusted in an acidic range with hydrochloric acid. After stirring for 30 minutes at 80° C the mixture was cooled to 20° C, the product precipitated was suction-filtered, washed neutral with water and dried at 100° C. Yield: 91% of the theory. Melting point of the anhydride: 283° C.

In analogy to Example 7, naphthalimide-4,5-dicarboxylic acids and the anhydrides thereof were prepared by using instead of the benzyl amine the equivalent amount of an amine indicated in Table 1 for the reaction. The corresponding dicarboxylic acids were obtained with a high purity and with a yield of 94 to 97.5% of the theory.

TABLE 1

| Ex. | Amine | Final product | melting point of the anhydride ° C |
|---|---|---|---|
| 8 | $H_2N$—⟨phenyl⟩—$CH_3$ | N-(4'-Methyl-phenyl)-naphthalimide-4,5-dicarboxylic acid | 269° |
| 9 | $H_2N$—⟨phenyl⟩—C(=O)$OCH_3$ | N-(4'-Carbomethoxy-phenyl)-naphthalimide-4,5-dicarboxylic acid | does not melt until 400° |
| 10 | $H_2N$—⟨phenyl⟩(Cl)—$OCH_3$ | N-(4'-Methoxy-5'-chloro-phenyl)-naphthalimide-4,5-dicarboxylic acid | 319° |
| 11 | $H_2N$—⟨phenyl⟩($CH_3$)—$OCH_3$ | N-(4'-Methoxy-3'-Methyl-phenyl)-naphthalimide-4,5-dicarboxylic acid | 315° |
| 12 | $H_2N$—⟨phenyl⟩($OCH_3$)—$OCH_3$ | N-(3',4'-Dimethoxy-phenyl)-naphthalimide 4,5-dicarboxylic acid | 313° |
| 13 | $NH_3$ | Naphthalimide-4,5-dicarboxylic acid | 387° |

EXAMPLE 14:

46.8 Grams of naphthalene-1,4,5,8-tetracarboxylic acid-anhydride were dissolved in 750 ml of water at 90°–95° C by addition of 85 g of a 33% sodium hydroxide solution. After addition of 25g of phosphoric acid (85% by weight) and 23 g of 4-amino-anisol the whole was refluxed for about 3 to 5 hours. The sodium salt of the N-(4'-methoxy-phenyl)-naphthalimide-4,5-dicarboxylic acid was formed which precipitated for the most part during the reaction. The imide-dicarboxylic acid was worked up as in Example 7. Yield: 94.5% of the theory. Melting point of the anhydride: 328° C.

EXAMPLE 15:

50 Grams of naphthalene-1,4,5,8-tetracarboxylic acid-semihydride were dissolved with the aid of 123 g of a 33% sodium hydroxide solution in 750 ml of water at 80° C; this solution was mixed with 50 g of a 85% phosphoric acid; stirring was continued for several minutes; after addition of 24.5 g of p-chloro-aniline the solution had a pH-value of 5.5. Then it was heated in the closed vessel up to 130° C and maintained for about 5 hours at this temperature, while stirring. The alkali salt of the N-(4'-chlorophenyl)-naphthalimide-4,5-carboxylic acid formed precipitated for the most part; it was completely free from naphthalene-tetracarboxylic acid. The sodium salt was worked up and converted into the free acid as described in Example 7. Yield: 95% of the theory. Melting point of the anhydride: 333° C.

EXAMPLE 16:

In analogous way as described in Example 15 the N-(4'-acetamino-phenyl)-naphthalimide-4,5-dicarboxylic acid-anhydride was prepared in a yield of more than 95% of the theory, if instead of p-chloroaniline 28.5 g of 4-amino-acetanilide were used as aniline derivative. The anhydride obtained melted only at a temperature superior to 390° C.

EXAMPLE 17:

If - in analogy to Example 15 - 21 g of phenylene-diamine were used as aniline component, the N-(4'-aminophenyl)-naphthalimide-4,5-dicarboxylic acid was obtained, when applying the same conditions of the process. Yield: 94% of the theory. After treating with π-chloro-naphthalene at 250° C according to the method described above, a compound was obtained which melted at a temperature of more than 400° C.

EXAMPLE 18:

A solution of 50 g of naphthalene-1,4,5,8-tetracarboxylic acid-semianhydride, 84 g of a 33% sodium hydroxide solution and 750 ml of water was heated up to 130° C after addition of 20 g of a 85% by weight phosphoric acid and 14 g of hydroxylamino-hydrochloride and maintained for about 5 hours in a closed vessel, while stirring, at this temperature. The sodium salt partly precipitated was worked up and converted into the N-hydroxy-naphthalimide-4,5-dicarboxylic acid in analogous was as described in Example 7. Yield: 90% of the theory. Melting point of the anhydride: 372° C.

EXAMPLE 19:

If, in analogous way as described in Example 18, 10 g of a 80% aqueous hydrazine-hydrate solution were added instead of hydroxyl amine, and if the operation was carried out in a closed vessel, the N-amino-naphthalimide-4,5-dicarboxylic acid was obtained after a reaction time of 4 to 5 hours and a temperature of 135° C after working up as described above, the yield being 88% of the theory.

The anhydride melted at a temperature of more than 400° C.

EXAMPLE 20:

50 Grams of naphthalene-1,4,5,8-tetracarboxylic acid-semianhydride were dissolved in 750 ml of water with the aid of 82 g of a 33% sodium hydroxide solution at 80° C. The solution was mixed with 20 g of a 85% phosphoric acid and 14 g of 3-aminopropanol-(1), a pH-value of 6.4 being adjusted. The solution was heated to 130° C in a closed vessel and maintained for about 5 hours at this temperature. After cooling to 60°-80° C, the undissolved naphthalene-tetracarboxylic aciddiimide formed was separated by filtration; the filtrate was adjusted to pH 2 with hydrochloric acid and stirred for 30 minutes at about 80° C. The N-(3'-hydroxy-n-propyl)-naphthalimide-4,5-dicarboxylic acid formed was suction-filtered after cooling the solution, washed free from salt and dried. Yield: 92% of the theory. Melting point of the anhydride: 278° C.

In analogy to the method described in Example 20, the following naphthalimide-4,5-dicarboxylic acids and the anhydrides thereof were obtained in a yield of more than 90% of the theory and with a high purity, when using the amines indicated in Table 2 in equivalent amounts.

TABLE 2

| Example | Amine | Final product | melting point ° C |
|---|---|---|---|
| 21 | $NH_2-CH_3$ | N-methyl-naphthalimide-4,5-dicarboxylic acid | 367° (Anhydride) |
| 22 | $H_2N-CH_2-CH_2-CH_2-COOH$ | N-(3'-carboxy-n-propyl)-naphthalimide-4,5-dicarboxylic acid | 210° (Anhydride) |
| 23 | $CH_3-(CH_2)_4-CH_2-NH_2$ | N-n-hexyl-naphthalimide-4,5-dicarboxylic acid | 180° (Anhydride) |
| 24 | $H_2N-(CH_2)_3-O-(CH_2)_2-OC_2H_5$ | N[(Ω-ethoxy-3'-ethoxy)-n-propyl]-naphthalimide-4,5-dicarboxylic acid | 135° |

EXAMPLE 25:

When the 3-methoxy-propylamine of Example 1 was replaced by 12 g of 3-(4'-hydroxy)-butoxy-propylamine, the N-(4''-hydroxy-3'-butoxy-propyl)-naphthalimide-4,5-dicarboxylic acid was obtained with a yield of 93% of the theory. Melting point: 143° C.

EXAMPLE 26:

50 Grams of naphthalene-1,4,5,8-tetracarboxylic acid were suspended in 750 ml of water and dissolved at 70° C with 82 g of NaOH (33%). After 10 minutes the pH-value was adjusted to 5.1 − 5.3 with 23 g of $H_3PO_4$ (85%) and the mixture was stirred after addition of 26 g of 3-amino-benzoic acid for 4 hours at 135° C. After cooling to 80° C the reaction product was partly precipitated, dissolved by addition of 1000 ml of water at 80° C, then it was filtered from a small amount of diimide formed. The filtrate was adjusted to pH 1.5 with hydrochloric acid at 70°-80° C and stirred for 30 minutes at 80° C.

The N-(3'-carboxy-phenyl)-naphthalimide-4,5-dicarboxylic acid was suction-filtered in the cold, washed with water and dried. Yield: 94% of the theory. Melting point of the anhydride: 362° C.

In analogous way naphthalimide-4,5-dicarboxylic acids were prepared, if instead of the 3-aminobenzoic acid the equivalent amount of one of the amines indicated in the following Table was used in the reaction. The corresponding dicarboxylic acids were obtained with a high purity and with a yield of 92 to 97% of the theory.

| Ex. | Amine | Final product | melting point of the anhydride |
|---|---|---|---|
| 27 | H₂N—⌬—COOH | N-(4'-carboxy-phenyl)-naphthalimide-4,5-dicarboxylic acid | >365° |
| 28 | Cl, H₂N—⌬—OCH₂, OCH₃ | N-(2'-chloro-4',5'-dimethoxy-phenyl)-naphthalimide-4,5-dicarboxylic acid | 190° |
| 29 | H₂N—⌬—C(O)—CH₃ | N-(4'-acetyl-phenyl)-naphthalimide-4,5-dicarboxylic acid | 322° |
| 30 | OC₂H₅, H₂N—⌬—Cl, OC₂H₅ | N-(4'-Cl-2',5'-diethoxy-phenyl)-naphthalimide-4,5-dicarboxylic acid | 193° |
| 31 | H₂N—CH₂—CH₂—NH₂ | N-(2'-amino-ethyl)-naphthalimide-4,5-dicarboxylic acid | >370° |

EXAMPLE 32:

If the operation was carried out as in Example 1 and if instead of the 3-methoxy-propylamine 6.6 g of N-methyl-1,3-diamino-propane were used, the hydrochloride of the N-(3-methylamino-n-propyl)-naphthalimide-4,5-di-carboxylic acid was obtained. Yield: 90.7% of the theory. Melting point: 280° C.

In analogous way as in Example 25, naphthalimide-4,5-dicarboxylic acids were prepared, if instead of the 4'-hydroxy-butoxy-propylamine the equivalent amount of an amine indicated in the following Table was used for the reaction.

The corresponding dicarboxylic acids were obtained with a high purity and in a yield of 90 to 97% of the theory.

| Ex. | Amine | Final product | Melting point of the anhydride |
|---|---|---|---|
| 33 | H₂N—⌬—C(O)—⌬ | N-(4'-benzoyl-phenyl) naphthalimide-4,5-dicarboxylic acid | 360° |
| 34 | H₂N—CH₂—C(=O)—OC₂H₅ | N-(carboethoxy-methyl)-naphthalimide-4,5-dicarboxylic acid | 247° |

We claim:
1. A compound of the formula

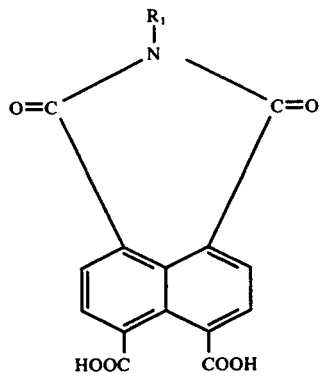

or the anhydride thereof, wherein $R_1$ is 3-(4'-hydroxy)-butoxypropyl.

* * * * *